US011384095B2

(12) United States Patent
Crockatt et al.

(10) Patent No.: US 11,384,095 B2
(45) Date of Patent: Jul. 12, 2022

(54) DIELS-ALDER REACTION WITH FURANICS TO OBTAIN AROMATICS

(71) Applicant: Nederlandse Organisatie voor toegepast-natuurwetenschappelijk onderzoek TNO, 's-Gravenhage (NL)

(72) Inventors: Marc Crockatt, 's-Hertogenbosch (NL); Johan Urbanus, 's-Gravenhage (NL); Pieter Cornelis Antonius Bruijnincx, Utrecht (NL); Christopher Stuart Lancefield, Dundee (GB); Bart Fölker, 's-Hertogenbosch (NL)

(73) Assignee: Nederlandse Organisatie Voor Toegepast-Natuurwetenschappelijk Onderzoek TNO, 's-Gravenhage (NL)

( * ) Notice: Subject to any disclaimer, the term of this patent is extended or adjusted under 35 U.S.C. 154(b) by 0 days.

(21) Appl. No.: 17/271,947

(22) PCT Filed: Aug. 29, 2019

(86) PCT No.: PCT/NL2019/050555
§ 371 (c)(1),
(2) Date: Feb. 26, 2021

(87) PCT Pub. No.: WO2020/046124
PCT Pub. Date: Mar. 5, 2020

(65) Prior Publication Data
US 2021/0323973 A1    Oct. 21, 2021

(30) Foreign Application Priority Data

Aug. 29, 2018 (EP) ..................... 18191392
Dec. 6, 2018 (EP) ..................... 18210798

(51) Int. Cl.
C07D 493/18 (2006.01)
C07D 307/89 (2006.01)
C07D 307/88 (2006.01)

(52) U.S. Cl.
CPC ......... *C07D 493/18* (2013.01); *C07D 307/88* (2013.01); *C07D 307/89* (2013.01)

(58) Field of Classification Search
CPC ... C07D 493/18; C07D 307/88; C07D 307/89
USPC ...................................... 549/298
See application file for complete search history.

(56) References Cited

U.S. PATENT DOCUMENTS

| 2,097,435 A | 11/1937 | Austin |
| 5,157,134 A | 10/1992 | Karanewsky |
| 2012/0116099 A1 | 5/2012 | Pfeffinger et al. |

FOREIGN PATENT DOCUMENTS

| CN | 104193759 A | 12/2014 |
| WO | 2017004349 A2 | 1/2017 |

OTHER PUBLICATIONS

Naguib et al., "Rapid, Regioselective Living Ring-Opening Metathesis Polymerization of Bio-Derivable Asymmetric Tricyclic Oxanorbornenes", Macromolecular Rapid Communications, 2018, 39, 5 pages.
Jung et al., "Studies on the Effects of Substituents on Rate Enhancements in Intramolecular Diels-Alder Reactions: Reasons for the GEM-Dimethyl Effect", Tetrahedron Letters, vol. 29, No. 20, 1988, pp. 2429-2432.
Imagawa et al., "A Synthetic Method for Novel 1,2,3-Trisubstituted Cyclopentane Derivatives, 1-Hydroxymethyl-3-Methoxy-2-Oxabicyclo [2.2.1' Heptane-7-Carboxylic Lactones", The Chemical Society of Japan Chemistry Letters, 1981, pp. 903-904.
Takano et al., "Diels-Alder Reaction of Furfural Derivatives and its Application", Pharmaceutical Institute, Tohoku University Aoba Aza Aramaki, Sendai, Jul. 1981, 9 pages.
Zaytsev et al., "Cycloaddition of Furfurylamines to Maleic Anhydride and its Substituted Derivatives", Chemistry of Heterocyclic Comp[unds, vol. 48, No. 3, Jun. 2012, pp. 505-513.
Folker, "Towards Biomass Derived Phthalic Anhydride via a Diels-Alder Route," Master Thesis Utrecht University, Jun. 2018, 109 pages.
Lin et al., "Phthalic Anhydride Production from Hemicellulose Solutions: Technoeconomic Analysis and Life Cycle Assessment," AIChe Journal vol. 61, No. 11, Nov. 2015, pp. 3708-3718.
Naguib et al., "Upporting Information; Rapid, Regioselective Living Ring-Opening Metathesis Polymerization of Bio-Derivable Asymmetric Tricyclic Oxanorbornenes," Macromol. Rapid Commun., 2018, 25 pages.

*Primary Examiner* — Kristin A Vajda
(74) *Attorney, Agent, or Firm* — BakerHostetler

(57) ABSTRACT

The present invention is directed to the preparation of phthalic anhydride compounds and the intermediate phthalide compounds. In particular, the invention is directed to an improved bio-based route from furanic compounds to phthalic anhydride compounds by reacting furfuryl alcohol (i.e. 2-hydroxymethylfuran) or an analogue thereof having a nucleophilic atom on the 2-methyl, with a dienophile comprising an α,β-unsaturated carbonyl comprising an α'-leaving group. The inventions further involved preparation of phthalic anhydride compounds, phthalic acid compounds and reduction products of the intermediate phthalide compounds.

20 Claims, No Drawings

DIELS-ALDER REACTION WITH FURANICS TO OBTAIN AROMATICS

CROSS-REFERENCE TO RELATED APPLICATIONS

This application is the National Stage of International Patent Application No. PCT/NL2019/050555, filed Aug. 29, 2019, which claims the benefit of EP Patent Application No. 18191392.2, filed Aug. 29, 2018 and EP Patent Application No. 18210798.7 filed Dec. 6, 2018, the disclosures of which are incorporated herein by reference in their entireties.

The invention is in the field of chemical processes. In particular, the invention is in the field of preparing aromatic compounds from bio-based furanic compounds.

In the recent years, interest in furanic compounds as intermediate chemical compounds for the production of chemicals from biomass has increased considerably. Of particular interest is the production of renewable aromatics from furanics by a cyclo-addition or Diels-Alder reaction with dienophiles. Depending on their specific substitution pattern, these aromatics can conveniently be used for production of a wide range of mass consumption products, such as plasticizers, synthetic fibers, (plastic bottles), fire-retardant materials, resins and the like. To this end, the reactions of a variety of different furanics with dienophiles have been investigated.

One target of interest is phthalide and its analogues and derivatives, such as phthalimides, phthalic diamides, phthalic anhydride and analogues, including phthalic acid and phthalate esters. One currently known bio-based route to phthalic anhydride involves the Diels-Alder reaction of furan (produced by decarbonylation of bio-based furfural, incurring CO loss) with maleic anhydride (Mahmoud, *Green Chemisty*, 16 (2014) 167-175). The produced Diels-Alder adduct can then be ring-opened and dehydrated using a mixture of methanesulfonic acid (expensive and difficult to recycle) and acetic anhydride, to produce phthalic anhydride. A drawback of this method is the poor atom economy, and a prohibitive processability and poor scalability of the final step resulting in a poor final yield. In addition, expensive, difficult to recycle regents are required.

The present inventors found an improved bio-based route from furanic compounds to phthalic anhydride compounds by reacting furfuryl alcohol (i.e. 2-hydroxymethylfuran) or an analogue thereof having a nucleophilic atom on the 2-methyl, with a dienophile comprising an α,β-unsaturated carbonyl comprising an α'-leaving group. Surprisingly, this reaction results in the clean formation of the phthalide as illustrated in Scheme 1, wherein the backbone of the furfuryl alcohol (i.e. 2-hydroxymethylfuran) or an analogue is illustrated by 'A', the nucleophilic atom by 'Nu', the dienophile by 'B', the α'-leaving group by 'LG' and the phthalide compound by 'D'.

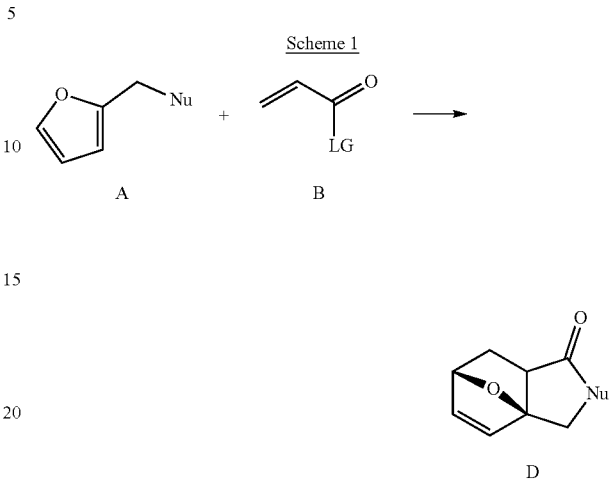

Scheme 1

Thus, unlike the typically expected formation of a complex mixture of regio- and stereoisomers, a single compound can be predominantly formed. Without wishing to be bound by theory, the inventors believe that the reaction of 'A' and 'B' proceeds by formation of intermediates 'C1' and 'C2' and that a further reaction of 'C2' provides a sink such that the reaction equilibrium is pulled to a predominant, single product (as illustrated in Scheme 2).

Scheme 2

Accordingly, in a preferred embodiment, the present invention is directed to a method for preparing a phthalide compound precursor according to structure IV, comprising reacting a furanic compound according to structure I with a dienophile according to structure II,

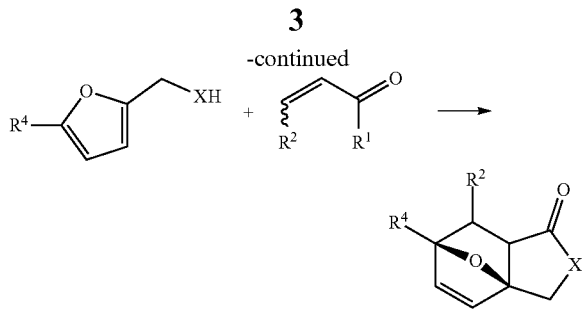

wherein
- X is selected from the group consisting of O, NH and S;
- $R^4$ is selected from H, Me, $CH_2OR^5$, $CH_2NR^5R^6$, CHO, $CO_2H$, $CO_2R_5$, $CONR^5R^6$, $CR^5=N-NR^5R^6$, wherein $R^5$ and $R^6$ are independently selected from H, $C_1$-$C_6$ alkyl, $C_6$-$C_{12}$ aryl, $C(O)R^7$, wherein $R^7$ is selected from alkoxy, for instance $C_1$-$C_6$ alkoxy, OH, $NH_2$ or a solid support, preferably H, Me, $CH_2OH$, CHO and $CO_2H$;
- $R^1$ is a leaving group selected from the group consisting of halide, O-EWG, NH-EWG and S-EWG, more preferably O-EWG, wherein EWG is an electron withdrawing group; and
- $R^2$ is selected from the group consisting of H, $C_1$-$C_6$ alkyl and $C(Y)R^3$, wherein
- Y is one or two selected from the group consisting of H, halide, O (e.g. =O) and combinations thereof, preferably H,
- $R^3$ is alkoxy, for instance $C_1$-$C_6$ alkoxy, OH, $NH_2$.

In the present context, in case a formula used herein comprises a chiral center of which the chirality is not indicated, said formula is meant to illustrate all variations of the chirality of said chiral center and concomitantly is meant to illustrate all individual stereoisomeric compounds and mixtures thereof. In addition, in case a formula used herein comprises a chiral center of which the chirality is indicated, this indication of the chirality is meant to illustrate the relative chirality of the chiral center with respect to other stereogenic centers within the same formula or compound, unless explicitly indicated otherwise. Thus, unless explicitly described otherwise, the structural formulae that illustrate the compounds described herein, illustrate both enantiomers of said compounds and/or diastereoisomers thereof, if applicable. Accordingly, for sake of completeness it is noted that the word 'compound' in reference to a particular formula, may refer to a plurality of compounds, i.e. a mixture of several isomers such as enantiomers or diastereoisomers. In general, part of the precursor IV will have the relative stereochemistry according to the structure below (wherein X is indicated as the oxygen O). However, the treatment with acid of base could cause this to change.

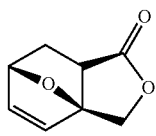

The wavy bond or squiggly bond symbol ⁓ in Formula II indicates that the stereochemistry of the double bond may be entgegen (E), or zusammen (Z), or a mixture thereof.

The leaving group $R^1$ typically comprises an electron-withdrawing group as this is believed to facilitate the lactonization (i.e. the reaction of the XH group and the $C(O)R^1$ group). Typical activated esters, anhydrides (both mixed or symmetrical), activated amides, activated thioesters, or acid halides as represented by the group consisting of halide, O-EWG, NH-EWG and S-EWG, wherein EWG is an electron withdrawing group are suitable. Activated esters include those typically used in peptide chemistry such as N-hydroxysuccinimide (NHS) esters and the like. The EWG can be known electron-withdrawing group such as a carbonyl, halide-substituted hydrocarbyls, nitrile-substituted hydrocarbyls, sulfonyl-substituted hydrocarbyls and nitro-substituted hydrocarbyls. A carbonyl as the EWG in O-EWG thus represents an anhydride as the dienophile. For instance, if EWG in O-EWG is acryloyl (i.e. $C(O)CH=CH_2$) and $R^2$ is H, the dienophile is the symmetrical acrylic anhydride. If EWG in O-EWG is formyl (i.e. $C(O)CH=CH_2$) and $R^2$ is H, the dienophile is the unsymmetrical (or mixed) acrylic formyl anhydride. A fluoride-substituted hydrocarbyl and/or a nitrophenol ester (e.g. 4-nitrophenol ester) is preferred as the EWG, as this is generally more electronegative than the alternatives. Examples of particularly preferred fluoride-substituted hydrocarbyls include 1,1,1,3,3,3-hexafluoroisopropyl or trifluoroethanol. The leaving group may optionally be linked to a solid support through suitable functionalization of the EWG.

With respect to the leaving group $R^1$, it was further found that the O-EWG group is particularly suitable for the furanic compounds I wherein XII is OH, thus for furfuryl alcohol type of furanic compounds. As such, the intermolecular Diels-Alder reaction is sufficiently fast with respect to the esterification of the XII and $C(O)R^1$, without compromising the lactonization, which is preferred as when esterification occurs prior to the Diels-Alder reaction, the Diels-Alder reaction has to proceed intramolecularly, which was found to be generally not possible or proceeds only very slowly. Surprisingly, it was also found that the furanic compounds wherein XII is $NH_2$, particularly $NH_9$, the leaving group can also suitably be a halide as the intramolecular Diels-Alder reaction be induced much more facile with respect to the furfuryl alcohol type of furanic compounds. However, an intermolecular Diels-Alder followed by lactamization may overall still be preferred.

As explained herein above more generally, the present inventors found that this reaction typically preferably proceeds through intermediate compounds IIIa and IIIb, and that XII likely intramolecularly reacts with the $C(O)R^1$ functionality in intermediate compound IIIa only.

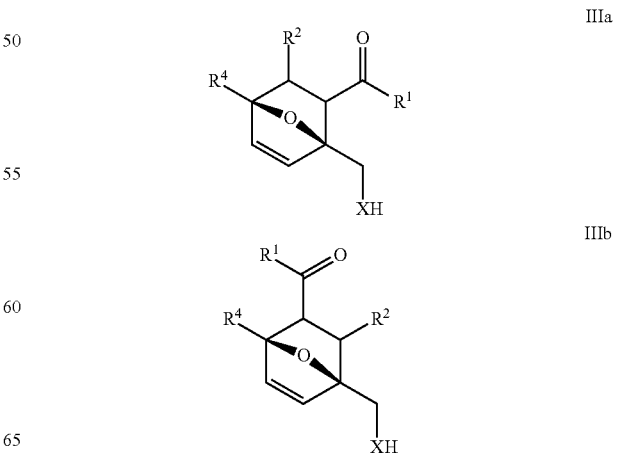

Generally, for sake of cost and energy efficiency, it is preferred to carry out the method of preparing the precursor according to structure IV in one single step and without isolation of one or more intermediate compounds such as compounds IIIa and/or IIIb. However, isolation of intermediate compound IIIa and/or intermediate compound IIIb, followed by further reacting said intermediate compound or compounds into the precursor according to structure IV is also regarded to be a particular embodiment of the present invention.

It was further found that the presence of a base when reacting the furanic and the dienophile is beneficial. Particularly, weak bases are preferred and weak bases having a $pK_b$ in water of between 2 and 12 are more preferred. Even more preferable the base has a $pK_b$ between 4 and 10, most preferably between 6 and 9. Examples of suitable bases included non-nucleophilic bases (which are preferred) such as bicarbonates, acetates, dichloroacetate and triethylamine with which all good yields have been obtained.

Another reaction condition of the method generally pertains contacting the furanic compound and the dienophile in a ratio of between 5:1 to 1:5, more preferably in a ratio between 2:1 to 1:2, most preferably in a ratio of about 1.1:1 to 1:1.1 such as about 1:1. The reaction of the furanic compound and the dienophile is typically carried out at a temperature below 200° C., more preferably below 130° C., most preferably in the range of 0 to 100° C.

To aid in the activation of the reaction, it may be preferred to carry out the method in a solvent. However, in alternative embodiments, reacting the furanic compound and the dienophile is carried out essentially neat or entirely neat.

The method of the present invention is preferably carried out in a continuous fashion. Reaction conditions, set-ups and reactors that may particularly be suitable in this respect may be those described in European patent application no. 18170098.0, which is herein incorporated in its entirety.

The phthalide compound precursor of the present invention is particular suitable to prepare a phthalide compound in accordance with formula V. This preparation comprises ring-opening and aromatization of the precursor according to structure IV.

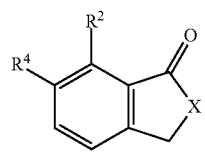

V

The ring-opening and aromatization can be carried out by contacting the precursor with an acid, including Brønsted and Lewis acids and soluble and solid acids, preferably an acid selected from the group consisting of methanesulfonic acid, sulfuric acid, acidic ion exchange resins, zeolites, optionally in combination with an activating agent. Typically, many acids will be suitable for this reaction due to the relative stability of the intermediate IV. Generally suitable conditions are those disclosed in European patent application no. 18170098.0 as well. The activating agent is selected from the group consisting of acylating agent, triflating agent, sulfonating agent, carbamylating agent, carbonylating agent, or combinations thereof, preferably the activating agent is an acylating agent, more preferably an acylating agent selected from the group consisting of acetic anhydride, acetyl chloride, propionic anhydride, butyric anhydride, isobutyric anhydride, trimethylacetic anhydride, mixed anhydrides thereof, or combinations thereof, most preferably the activating agent comprises acetic anhydride.

Alternatively to the use of an acid, the precursor can be ring-opened with base (i.e. by deprotonation of the proton alpha to the lactone carbonyl in IV).

In a particular embodiment of the present invention, the phthalide compound is oxidized to phthalic anhydride compound according to formula VI using conventional methods, such as those processes including nitric acid, those conditions known in the Amoco process, enzymatic oxidation, electrochemical oxidation, and the like. The phthalic anhydride compound according to formula VI can subsequently be hydrolyzed to phthalic acid compound according to formula VII, or esters, amides and imides thereof using conventional methods. Alternatively, these processes can be carried out vice-versa: phthalide compound of formula V can first be hydrolyzed, which can be followed by oxidation and derivatization to result in the phthalic acid compound and its derivatives.

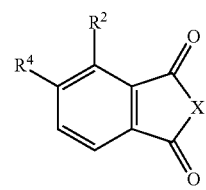

VI

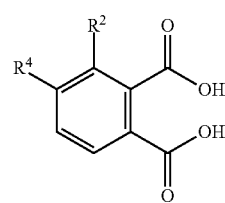

VII

In a particular embodiment of the present invention, the phthalide compound precursor is reduced instead of oxidized as described above. Reduction can for instance result in any of compounds IIX and IX.

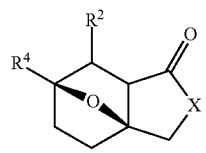

IIX

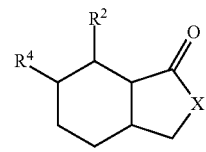

IX

Typical reduction conditions include those for hydrogenation using a known catalyst such as Pd/C. According to the present invention, the phthalide compound precursor may also be used to prepare any of the compounds X, XI, XII and XIII.

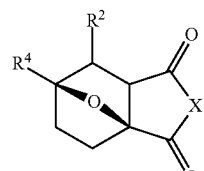
X
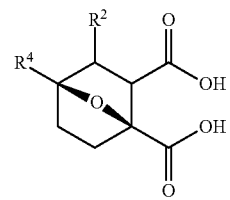
XII
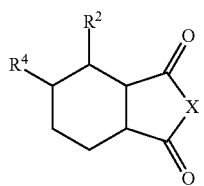
XI
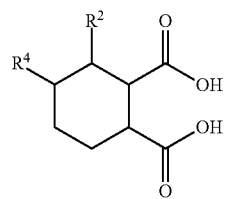
XIII
In general, the present method allows the preparation of the compounds V, VI, IIX, IX, X and XI from compound IV according to the following Scheme 3.
Scheme 3
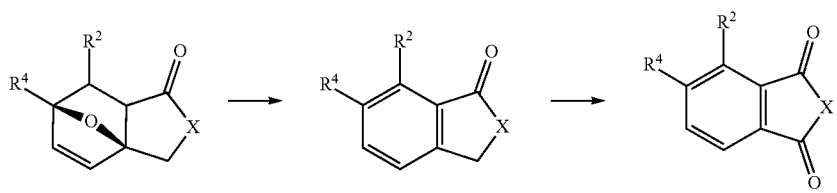
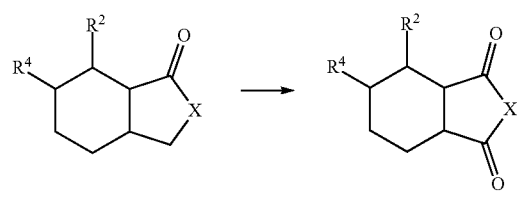

For example, the above-mentioned compounds X, XI, XII and XIII can be obtained by a method comprising oxidation of the compound in accordance with formula IIX (resulting in the compound of formula X), oxidation of the compound in accordance with formula IX (resulting in the compound of formula XI), oxidation and then reduction of the compound in accordance with formula IIX (resulting in the compound of formula XI, see also WO/2016099275); oxidation of the compound in accordance with formula IIX followed by hydrolysis (resulting in the compound of formula XII) or oxidation of the compound in accordance with formula IIX followed by hydrolysis (resulting in the compound of formula XIII).

For sake of clarity and conciseness, in the context of the present invention, the phthalide compound precursors are collectively referred to with the term phthalide, even if X may also include NH or S (besides O) in formula IV. Similarly, the phthalide compound according to formula V that may be obtained from said precursor includes compound wherein X is NH or S (besides O). Thus, the term phthalide compound includes phthalimides and thiophthalide and the like. The same applies to, mutatis mutandis, the phthalic anhydride compounds disclosed herein.

As used herein, the singular forms "a", "an" and "the" are intended to include the plural forms as well, unless the context clearly indicates otherwise. The term "and/or" includes any and all combinations of one or more of the associated listed items. It will be understood that the terms "comprises" and/or "comprising" specify the presence of stated features but do not preclude the presence or addition of one or more other features.

For the purpose of clarity and a concise description features are described herein as part of the same or separate embodiments, however, it will be appreciated that the scope of the invention may include embodiments having combinations of all or some of the features described.

The present invention can be illustrated by the following examples.

EXAMPLE 1—1,1,1,3,3,3-HEXAFLUOROISOPROPYLACRYLATE

A suspension of 1,1,1,3,3,3-hexafluoroisopropanol (49.91 g, 297 mmol, 1.2 eq.) and scandium(III) triflate (0.10 g, 0.20 mmol, 0.08 mol %) were stirred at 20° C. and acryloyl chloride (22.40 g, 248 mmol, 1 eq.) was added dropwise over the course of 5 minutes. After stirring the mixture for 20 hours at 20° C., sodium bicarbonate was added to the stirred suspension until pH>7 was achieved. The solids were removed by filtration, and filtrates were distilled under nitrogen to yield the desired product.

EXAMPLE 2—7,7A-DIHYDRO-3H-3A,6-EPOXY-ISOBENZOFURAN-1(6H)-ONE

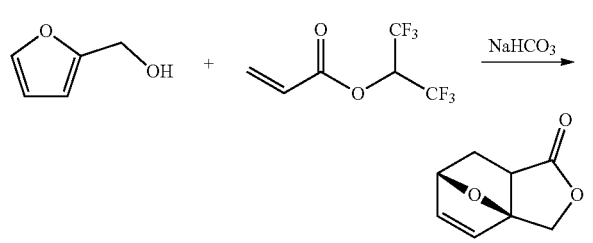

A suspension of furfuryl alcohol (1 eq.), 1,1,1,3,3,3-hexafluoroiso-propylacrylate (1.1 eq.) and sodium bicarbonate (1 mol %) was stirred at 80° C. for 22 hours then the mixture was cooled to 20° C. and the product was isolated as a solid (64% yield) following flash chromatography.

EXAMPLE 3—7,7A-DIHYDRO-3H-3A,6-EPOXY-ISOBENZOFURAN-1(6H)-ONE

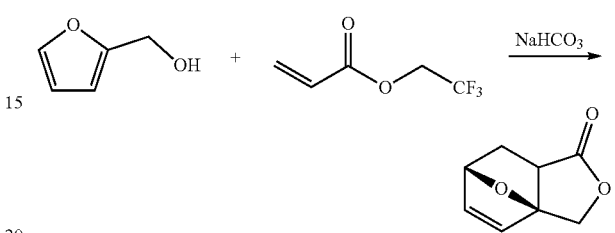

A suspension of furfuryl alcohol (1 eq.), 1,1,1-trifluoroethylacrylate (1 eq.) and sodium bicarbonate (20 mol %) were stirred at 80° C. for 22 hours. This yielded 7,7a-Dihydro-311-3a,6-epoxyisobenzofuran-1(6H)-one (33% yield, 39% selectivity).

EXAMPLE 4—7,7A-DIHYDRO-3H-3A,6-EPOXY-ISOBENZOFURAN-1(6H)-ONE

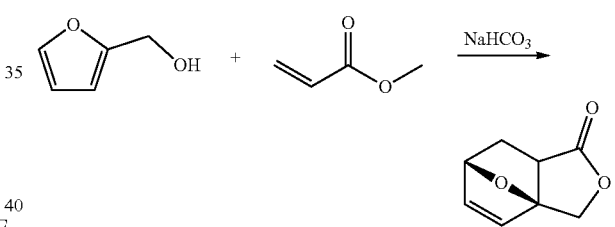

A suspension of furfuryl alcohol (1 eq.), methyl acrylate (1 eq.) and sodium bicarbonate (20 mol %) were stirred at 80° C. for 22 hours. This yielded 7,7a-Dihydro-311-3a,6-epoxyisobenzofuran-1(6H)-one (2% yield, 8% selectivity).

EXAMPLE 5—7,7A-DIHYDRO-3H-3A,6-EPOXY-ISOBENZOFURAN-1(6H)-ONE

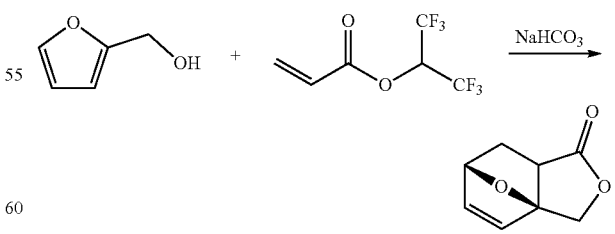

A suspension of furfuryl alcohol (1 eq.), 1,1,1,3,3,3-hexafluoroiso-propylacrylate (1.5 eq.) and sodium bicarbonate (20 mol %) was stirred at 80° C. for 22 hours. This yielded 7,7a-Dihydro-311-3a,6-epoxyisobenzofuran-1(6H)-one (68% yield, 88% selectivity).

EXAMPLE 6—7,7A-DIHYDRO-3H-3A,6-EPOXY-ISOBENZOFURAN-1(6H)-ONE

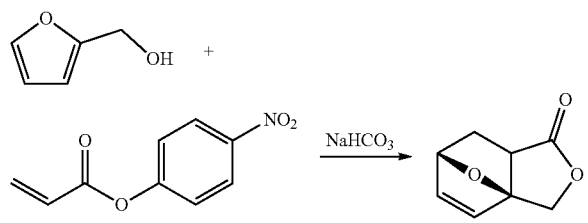

A suspension of furfuryl alcohol (1 eq.), 4-nitrophenol acrylate (1.1 eq.) and sodium bicarbonate (2 mol %) was stirred at 80° C. for 36 hours. This yielded 7,7a-Dihydro-3H-3a,6-epoxyisobenzofuran-1(6H)-one (86% yield, 91% selectivity).

EXAMPLE 7—7,7A-DIHYDRO-3H-3A,6-EPOXY-ISOBENZOFURAN-1(6H)-ONE

A suspension of furfuryl alcohol (1 eq.) and acrylic anhydride (1 eq.) were stirred at 45° C. for 16 hours. This yielded 7,7a-Dihydro-3H-3a,6-epoxyisobenzofuran-1(6H)-one (43% yield, 44% selectivity).

EXAMPLE 8—SCREENING OF CONDITIONS FOR DIELS-ALDER LACTONISATION to 7,7a-Dihydro-3H-3a,6-epoxyisobenzofuran-1(6H)-one

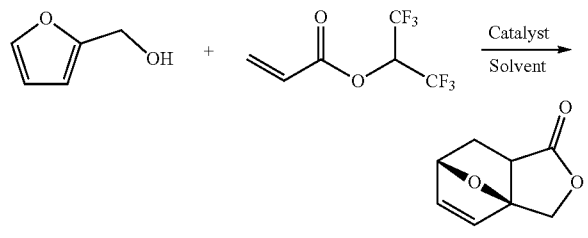

A mixture of furfuryl alcohol (1 eq.), 1,1,1,3,3,3-hexafluoroiso-propylacrylate (1 eq.), catalyst (see Table X) and solvent (see Table 1; concentration=1.1 M) was stirred at the stated temperature (see Table 1). The results of these reactions are shown in Table 1.

TABLE 1

| Solvent | Cat. | mol % Cat. | T (° C.) | Yield (%) | Selectivity (%) |
|---|---|---|---|---|---|
| Neat | NaHCO₃ | 2 | 60 | 34 | 43 |
|  |  | 20 | 60 | 17 | 20 |
|  |  | 0.5 | 80 | 38 | 70 |
|  |  | 1 | 80 | 64 | 82 |
|  |  | 2 | 80 | 54 | 66 |
|  |  | 20 | 80 | 26 | 28 |
|  | NaCH₃CO₂ | 2 | 80 | 44 | 55 |
|  |  | 20 | 80 | 23 | 27 |
|  | NaCHCl₂CO₂ | 2 | 80 | 31 | 50 |
|  |  | 20 | 80 | 45 | 58 |
|  | NEt₃ | 2 | 80 | 30 | 34 |
| EtOAc | NaHCO₃ | 2 | 80 | 43 | 83 |

EXAMPLE 9—SCREENING OF ACID CONDITIONS FOR AROMATIZATION TO PHTHALIDE

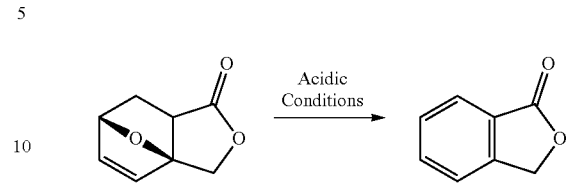

The lactone (1 eq.) is added to a stirred solution of the desired acid (See Table Y), in solvent (where applicable—See Table 2—all reactions with solvent performed at 0.33 M) at 20° C., then the mixture is heated to the stated temperature (see Table 2) for 1 hour. The results of these reactions are shown in Table Y.

TABLE 2

| Solvent | Cat. | T (° C.) | Yield (%) |
|---|---|---|---|
| Neat | MSA* (13 eq.) | 20 | 66 |
| Toluene | MSA (0.1 eq.) | 80 | 66 |
|  | Hf(OTf)₄ (0.1 eq.) | 80 | 60 |
|  | TfOH (0.1 eq.) | 80 | 63 |
|  | TfOH (0.01 eq.) | 80 | 63 |
|  | Silica-TfOH (0.01 eq.) | 80 | 58 |
| CHCl₃ | TfOH (0.1 eq.) | 80 | 79 |
| AcOH | TfOH (0.1 eq.) | 80 | 56 |

*MSA: methanesulfonic acid

EXAMPLE 10—SCREENING OF DRY, ASSISTED ACID CONDITIONS FOR AROMATIZATION TO PHTHALIDE

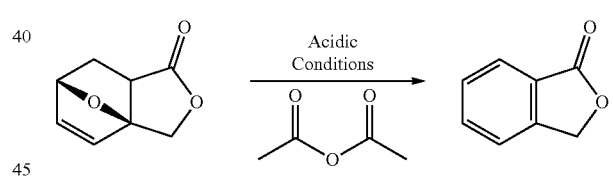

The lactone (1 eq.) is added to a stirred solution of the desired acid (See Table Z) and acetic anhydride (See Table Z), in solvent (where applicable—See Table Z—all reactions with solvent performed at 1 M), at 20° C., then the mixture is heated to the stated temperature (see Table 3). The results of these reactions are shown in Table 3.

TABLE 3

| Solvent | Cat. | Ac₂O | T (° C.) | Yield (%) |
|---|---|---|---|---|
| Neat | MSA (13 eq) | 20 vol % | 20 | 75 |
|  | MSA (0.5 eq.) | 4 eq. | 20 | 97 |
|  | MSA (0.5 eq.) | 4 eq. | 80 | 98 |
|  | MSA (0.1 eq.) | 4 eq. | 80 | 95 |
|  | MSA (0.02 eq.) | 4 eq. | 80 | 94 |
|  | MSA (0.01 eq.) | 4 eq. | 80 | 39 |
|  | TfOH (0.01 eq.) | 4 eq. | 80 | 95 |
|  | H₂SO₄ (0.01 eq.) | 4 eq. | 80 | 80 |
|  | Amberlyst-15 (0.1 eq) | 4 eq. | 80 | 82 |
| EtOAc | Amberlyst-15 (0.1 eq) | 4 eq. | 80 | 78 |
|  | Amberlyst-15 (0.1 eq) | 2 eq. | 80 | 89 |

EXAMPLE 11—7-METHYL-3,10-DIOXATRICYCLO[5.2.1.0]DEC-8-EN-4-ONE

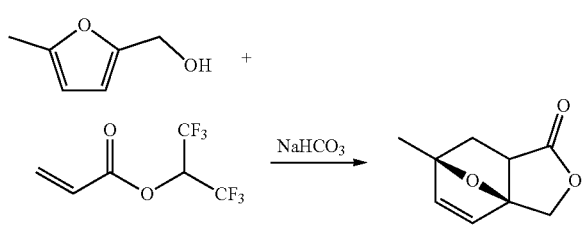

A suspension of 5-methylfurfuryl alcohol (1 eq.), 1,1,1,3,3,3-hexafluoroiso-propylacrylate (1 eq.) and sodium bicarbonate (1 mol %) were stirred at 80° C. for 22 hours. This yielded 7-methyl-3,10-dioxatricyclo[5.2.1.0]dec-8-en-4-one (74% yield) as a solid following flash chromatography. The structure was confirmed by nuclear magnetic resonance (NMR) and by X-ray crystallography.

EXAMPLE 12—7-METHYL-3,10-DIOXATRICYCLO[5.2.1.0]DEC-8-EN-4-ONE

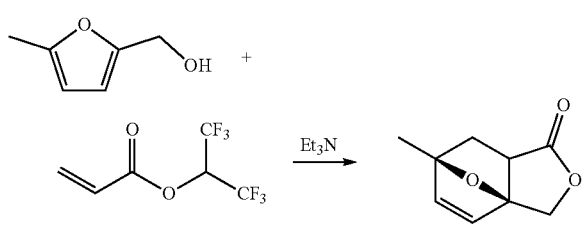

A solution of 5-methylfurfuryl alcohol (1 eq.), 1,1,1,3,3,3-hexafluoroiso-propylacrylate (1 eq.) and triethylamine (1 mol %) were stirred at 80° C. for 24 hours. This yielded a mixture of 7-methyl-3,10-dioxatricyclo[5.2.1.0]dec-8-en-4-one and 5-methylfurfuryl alcohol in a 3:5 ratio. The structure was confirmed by NMR.

EXAMPLE 13—7,7A-DIHYDRO-3H-3A,6-EPOXYISOBENZOFURAN-1(6H)-ONE

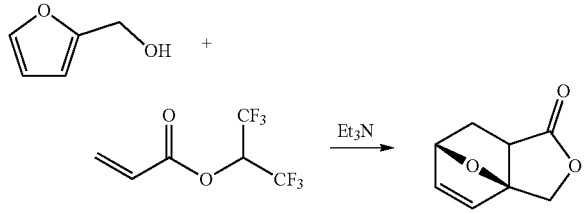

A solution of furfuryl alcohol (1 eq.), 1,1,1,3,3,3-hexafluoroiso-propylacrylate (1 eq.) and triethylamine (1 mol %) were stirred at 80° C. for 24 hours. This yielded a mixture of 7,7a-dihydro-311-3a,6-epoxyisobenzofuran-1(6H)-one and furfuryl alcohol in a 3:2 ratio. The structure was confirmed by NMR.

EXAMPLE 14—TETRAHYDRO-3H-3A,6-EPOXYISOBENZOFURAN-1(4H)-ONE

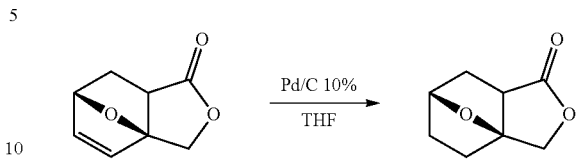

A suspension of 7,7a-dihydro-311-3a,6-epoxyisobenzofuran-1(6H)-one (1 eq.) and 10% palladium on carbon (20 mg/g substrate) in 2-methyltetrahydrofuran (5 ml/g substrate) was pressuried to 15 bar with hydrogen and then stirred for 16 hours at 20° C. The catalyst was removed by filtration, and the solvent removed by reduced pressure evaporation. This yielded tetrahydro-311-3a,6-epoxyisobenzofuran-1(4H)-one (quantitative yield) as an oil. The structure was confirmed by NMR.

EXAMPLE 15—7-METHYL-3,10-DIOXATRICYCLO[5.2.1.0]DECAN-4-ONE

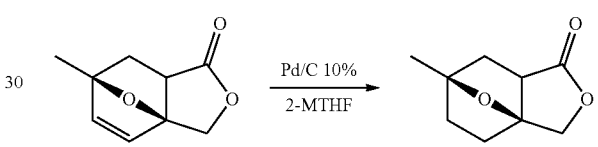

A suspension of 7-methyl-3,10-dioxatricyclo[5.2.1.0]dec-8-en-4-one (1 eq.) and 10% palladium on carbon (20 mg/g substrate) in 2-methyltetrahydrofuran or methanol (5 ml/g substrate) was pressuried to 15 bar with hydrogen and then stirred for 16 hours at 20° C. The catalyst was removed by filtration, and the solvent removed by reduced pressure evaporation. This yielded 7-methyl-3, 10-dioxatricyclo[5.2.1.0]decan-4-one (quantitative yield) as an oil. The structure was confirmed by NMR.

EXAMPLE 16—1,6,7,7A-TETRAHYDRO-1-OXO-3H-3A,6-EPOXYISOBENZOFURAN-7-CARBOXYLIC ACID

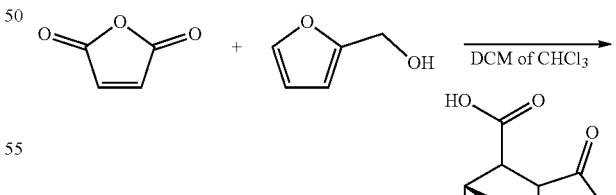

A solution of furfuryl alcohol (1 eq.) and maleic anhydride (1 eq.) in dichloromethane or chloroform (3.1 ml/g furfuryl alcohol) was stirred at 20° C. for 24 hours, to yield a slurry. The solid was isolated by filtration, then slurried in tetrahydrofuran (1 ml/g of solid). After stirring for 30 minutes the solid was isolated by filtration, washed, and dried. This yielded 1,6,7,7a-tetrahydro-1-oxo-3H-3a,6-epoxyisobenzofuran-7-carboxylic acid (52% and 55% respectively) as a solid. The structure was confirmed by NMR.

EXAMPLE 17—HEXAHYDRO-1-OXO-3H-3A,6-EPOXYISOBENZOFURAN-7-CARBOXYLIC ACID

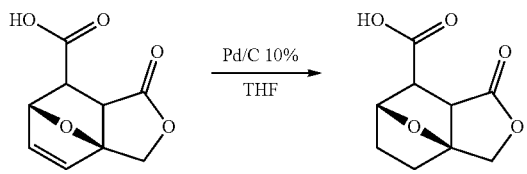 [SMILES: O=C(O)C1C2C(=O)OC[C@]23C=C[C@H]1O3 ; O=C(O)C1C2C(=O)OC[C@]23CC[C@H]1O3 ; "THF"]

A suspension of 1,6,7,7a-tetrahydro-1-oxo-3H-3a,6-epoxyisobenzofuran-7-carboxylic acid (1 eq.) and 10% palladium on carbon (20 mg/g substrate) in tetrahydrofuran or methanol (5 ml/g substrate) was pressurised to 15 bar with hydrogen and then stirred for 16 hours at 20° C. When THF was used, methanol was added after reaction to solubilize the product. The catalyst was removed by filtration, and the solvent removed by reduced pressure evaporation. This yielded hexahydro-1-oxo-3H-3a,6-epoxyisobenzofuran-7-carboxylic acid (81.9% and 84.1% yield respectively) as a solid. The structure was confirmed by NMR.

EXAMPLE 18—1,3-DIHYDRO-3-OXO-4-ISOBENZOFURANCARBOXYLIC ACID & PHTHALIDE

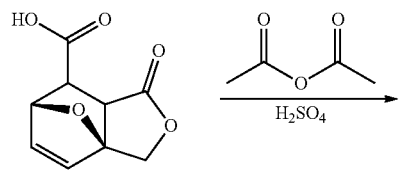

1,6,7,7a-tetrahydro-1-oxo-3H-3a,6-epoxyisobenzofuran-7-carboxylic acid (1 eq.) is added to a stirred solution of sulfuric acid (0.5 eq.) and acetic anhydride (4 eq.) at 0° C. After complete addition, the mixture was heated to 45° C. and held for 14 hours, then cooled to 0° C. The resulting solids were isolated by filtration (50 wt %). This was shown to be a mixture of 1,3-dihydro-3-oxo-4-Isobenzofurancarboxylic acid and phthalide in a 1:1 ratio. The filtrates were quenched with water and then extracted with DCM. The organics were dried and then concentrated by reduced pressure evaporation. This yielded 1,3-dihydro-3-oxo-4-isobenzofurancarboxylic acid (23.2% yield) as a solid. The structure was confirmed by NMR.

EXAMPLE 19-6-METHYLPHTHALIDE

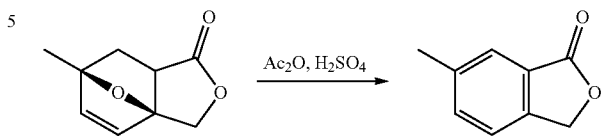

7-methyl-3,10-dioxatricyclo[5.2.1.0]dec-8-en-4-one (1 eq.) was added over 15 minutes to a stirred solution of acetic anhydride (4 eq.) and sulfuric acid (0.5 eq.) at 0° C. After complete dissolution, the mixture was heated to 60° C. and held for 2 hours. Analysis by NMR confirmed a clean, quantitative conversion to 6-methylphthalide.

EXAMPLE 20—6-METHYL-3,10-DIOXATRICYCLO[5.2.1.0]DEC-8-EN-4-ONE

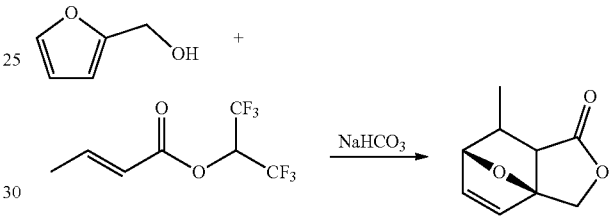

A solution of furfuryl alcohol (1 eq.), 1,1,1,3,3,3-hexafluoroisopropyl crotonate (1 eq.) and sodium bicarbonate (1 mol %) were stirred at 80° C. for 22 hours. This yielded 6-methyl-3,10-dioxatricyclo[5.2.1.0]dec-8-en-4-one as a liquid following flash chromatography. The structure was confirmed by NMR.

The invention claimed is:
1. A method for preparing a phthalide compound precursor according to formula IV, comprising reacting a furanic compound according to formula I with a dienophile according to formula II:

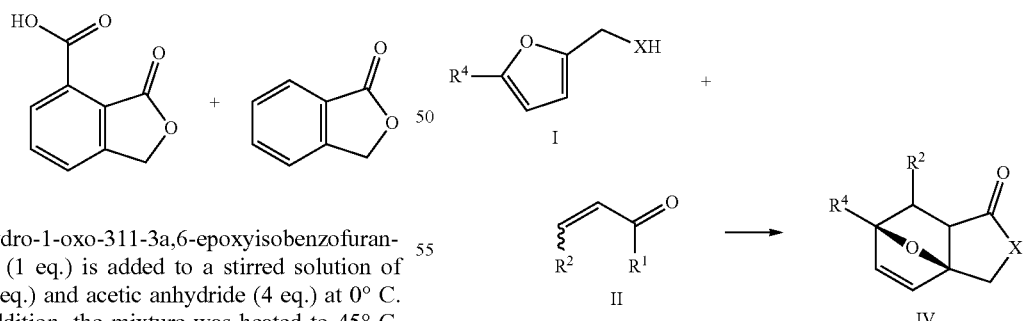

wherein:
X is selected from the group consisting of O, NH and S;
$R^4$ is selected from the group consisting of H, Me, $CH_2OR^5$, $CH_2NR^5R^6$, CHO, $CO_2R_5$, $CONR^5R^6$, and $CR^5$=N—$NR^5R^6$, wherein
$R^5$ and $R^6$ are independently selected from the group consisting of H, $C_1$-$C_6$ alkyl, $C_6$-$C_{12}$ aryl, and C(O)

R⁷, wherein R⁷ is selected from the group consisting of alkoxy, OH, NH₂ and a solid support;

R¹ is a leaving group selected from the group consisting of halide, O-EWG, NH-EWG and S-EWG, wherein EWG is an electron withdrawing group; and R² is selected from the group consisting of H, $C_1$-$C_6$ alkyl and C(Y)R³, wherein Y is one or two selected from the group consisting of H, halide, O and combinations thereof, R³ is alkoxy, OH, NH₂, or SH.

2. The method according to claim 1, wherein X is O, R⁴ is H, and/or R² is H.

3. The method according to claim 1, wherein the EWG is selected from the group consisting of carbonyls, halide-substituted hydrocarbyls, nitrile-substituted hydrocarbyls, sulfonyl-substituted hydrocarbyls and nitro-substituted hydrocarbyls, optionally linked to a solid support.

4. The method according to claim 1, comprising reacting the furanic and the dienophile in the presence of a base.

5. The method according to claim 1, comprising contacting the furanic compound and the dienophile in a ratio of between 5:1 to 1:5.

6. The method according to claim 1, comprising reacting the furanic compound and the dienophile at a temperature below 200° C.

7. The method according to claim 1, comprising reacting the furanic compound according to formula I with the dienophile according to formula II through intermediate compound IIIa and/or intermediate compound IIIb

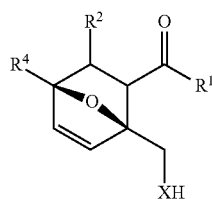

IIIa

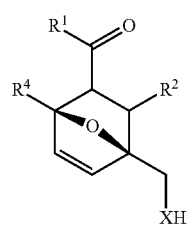

IIIb

8. The method according to claim 7, that is carried out in one single step and without isolating one or more intermediate compounds.

9. The method according to claim 7, comprising isolating intermediate compound IIIa and/or intermediate compound IIIb, followed by reacting said intermediate compound or intermediate compounds to the precursor according to formula IV.

10. A method for preparing a compound according to formulae V, VI, VII, IIX, IX, X, XI, XII or XIII, or an ester, amide or imide thereof:

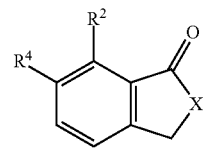

V

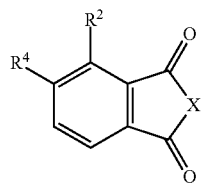

VI

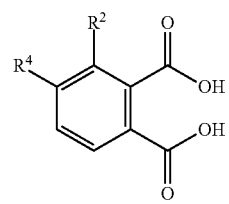

VII

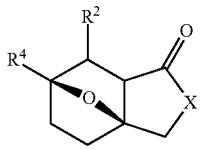

IIX

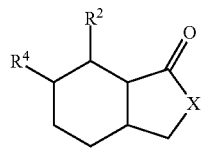

IX

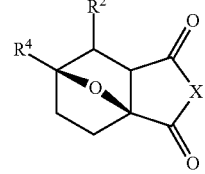

X

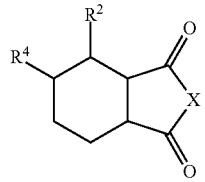

XI

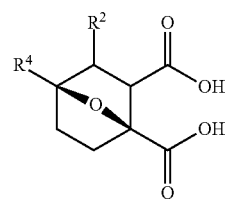

XII

XIII

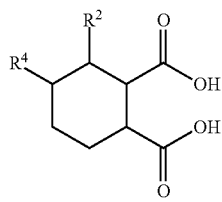

comprising reacting a precursor of formula IV in one or more further reactions, wherein the precursor of formula IV is prepared using the method according to claim 1.

11. The method according to claim 10, further comprising ring-opening and aromatizing the precursor of formula IV by contacting the precursor of formula IV with an acid, optionally in combination with an activating agent to provide the phthalide compound of formula V

V

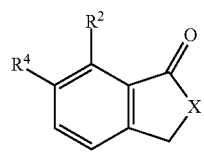

12. The method according to claim 11, further comprising oxidizing said phthalide compound according to formula V to provide the phthalic anhydride compound according to formula VI

VI

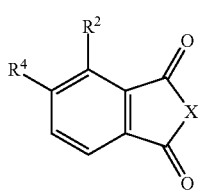

13. The method according to claim 12, further comprising hydrolyzing said phthalic anhydride compound according to formula VI or formula V followed by oxidizing

VII

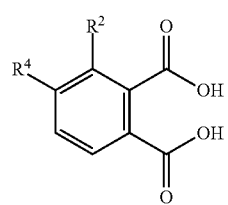

14. The method of claim 1, further comprising reducing the phthalide analogue precursor according to formula IV to provide a compound according to formula IIX and/or IX

IIX

IX

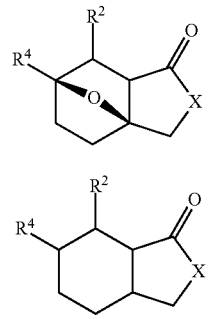

15. The method according to claim 14, further comprising:
  oxidizing the compound according to formula IIX to provide a compound according to formula X;
  oxidizing the compound according to formula IX to provide a compound according to formula XI;
  oxidizing and then reducing the compound according to formula IIX to provide a compound according to formula XI;
  oxidizing the compound according to formula IIX followed by hydrolyzing to provide a compound according to formula XII; or
  oxidizing the compound according to formula IX followed by hydrolyzing to provide a compound according to formula XIII

X

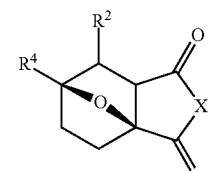

XI

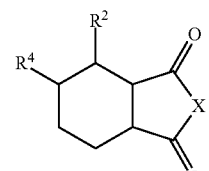

XII

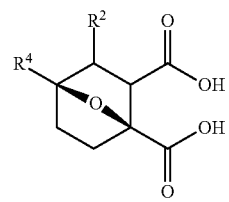

XIII

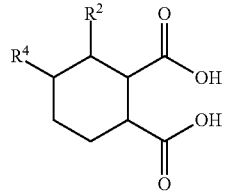

16. A compound of formulae IIIa, IIIb, IIX, IX, X, XI, XII or XIII or an ester, amide or imide thereof

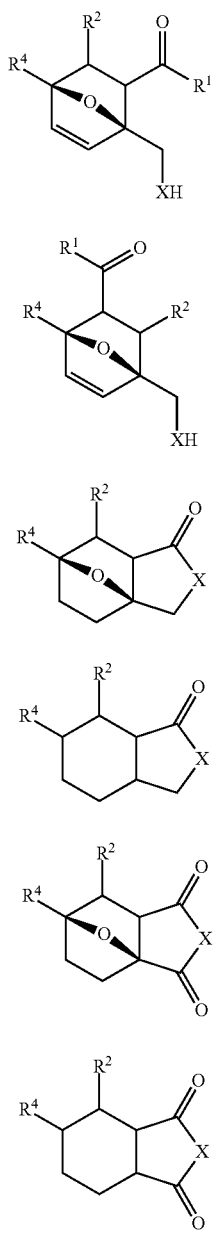

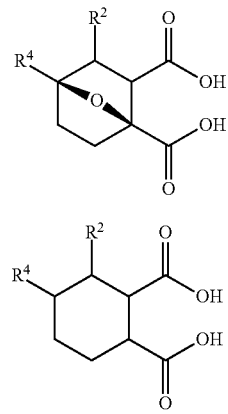

wherein:
X is selected from the group consisting of O, NH and S;
$R^4$ is selected from the group consisting of H, Me, $CH_2OR^5$, $CH_2NR^5R^6$, CHO, $CO_2R_5$, $CONR^5R^6$, and $CR^5=N-NR^5R^6$, wherein
$R^5$ and $R^6$ are, independently, selected from the group consisting of H, $C_1$-$C_6$ alkyl, $C_6$-$C_{12}$ aryl, and C(O)$R^7$, wherein $R^7$ is selected from the group consisting of alkoxy, OH, $NH_2$ and a solid support;
$R^1$ is a leaving group selected from the group consisting of halide, O-EWG, NH-EWG and S-EWG, wherein EWG is an electron withdrawing group; and
$R^2$ is selected from the group consisting of H, $C_1$-$C_6$ alkyl and $C(Y)R^3$, wherein
Y is one or two selected from the group consisting of H, halide, O and combinations thereof,
$R^3$ is alkoxy, OH, $NH_2$, or SH;
wherein only one of $R^2$ and $R^4$ is H when the compound is of formula XI and X is O.

17. The method according to claim 1, wherein (i) $R^1$ is O-EWG; or (ii) Y is H.

18. The method according to claim 3, wherein the EWG is (i) a fluoride-substituted hydrocarbyl or (ii) 1, 1, 1,3,3,3-hexafluoroisopropyl or trifluoroethanol.

19. The method according to claim 11, wherein the acid is selected from the group consisting of methanesulfonic acid, sulfuric acid, an acidic ion exchange resin, and a zeolite.

20. The method according to claim 11, wherein the activating agent is acetic acid.

* * * * *